United States Patent [19]

Mizumoto et al.

[11] Patent Number: 5,576,014
[45] Date of Patent: Nov. 19, 1996

[54] INTRABUCCALLY DISSOLVING COMPRESSED MOLDINGS AND PRODUCTION PROCESS THEREOF

[75] Inventors: Takao Mizumoto; Yoshinori Masuda; Muneo Fukui, all of Shizuoka, Japan

[73] Assignee: Yamanouchi Pharmaceutical Co., Ltd, Tokyo, Japan

[21] Appl. No.: 385,093

[22] Filed: Feb. 1, 1995

Related U.S. Application Data

[63] Continuation-in-part of Ser. No. 351,118, Nov. 30, 1994, abandoned.

[30] Foreign Application Priority Data

Jan. 31, 1994 [JP] Japan ................................. 6-10112
Apr. 25, 1994 [JP] Japan ................................. 6-86652

[51] Int. Cl.⁶ ........................................ A61F 13/00
[52] U.S. Cl. ........................ 424/435; 424/456; 424/465; 424/486
[58] Field of Search ............................. 424/435, 456, 424/465, 486

[56] References Cited

U.S. PATENT DOCUMENTS

| | | | |
|---|---|---|---|
| 4,572,832 | 2/1986 | Kigasawa et al. | 514/772.1 |
| 4,764,378 | 8/1988 | Keith et al. | 424/435 |
| 5,039,540 | 8/1991 | Ecanow | 426/385 |
| 5,135,752 | 8/1992 | Snipes | 424/435 |

FOREIGN PATENT DOCUMENTS

| | | |
|---|---|---|
| 0553777 | 8/1993 | European Pat. Off. . |
| 5271054 | 10/1993 | Japan . |
| 5310558 | 11/1993 | Japan . |

*Primary Examiner*—Thurman K. Page
*Assistant Examiner*—William E. Benston, Jr.
*Attorney, Agent, or Firm*—Sughrue, Mion, Zinn, Macpeak & Seas

[57] ABSTRACT

Intrabuccally dissolving compressed moldings comprising a saccharide having low moldability having been granulated with a saccharide having high moldability. The moldings of the present invention show quick disintegration and dissolution in the buccal cavity and have an adequate hardness.

33 Claims, No Drawings

INTRABUCCALLY DISSOLVING COMPRESSED MOLDINGS AND PRODUCTION PROCESS THEREOF

This is a continuation-in-part application of application Ser. No. 08/351,118, filed Nov. 30, 1994, now abandoned.

FIELD OF THE INVENTION

The present invention relates to intrabuccally dissolving compressed moldings which quickly disintegrate and dissolve in the buccal cavity and have an adequate hardness and to production processes thereof. Particularly, the present invention relates to intrabuccally dissolving compressed moldings which are useful in the pharmaceutical field.

The term "intrabuccally dissolving compressed moldings" as used herein means compressed moldings which show practically sufficient disintegration and dissolution by saliva by merely keeping in the mouth without holding water in the buccal cavity and which have adequate hardness. The term "practically sufficient disintegration and dissolution" as used herein means that the moldings disintegrate or dissolve in the buccal cavity within approximately 1 to 120 seconds, preferably within approximately 1 to 60 seconds, and more preferably within approximately 1 to 40 seconds. The term "adequate hardness" means that the moldings have a sufficient hardness so that the molding do not break during the production steps and distribution stages.

BACKGROUND OF THE INVENTION

Dosage forms in which easy swallowing by patients is taken into consideration are scarce in spite of the existence of various known dosage forms of pharmaceutical preparations for oral administration use. Accordingly, great concern has been directed toward the development of a dosage form which can easily be handled, especially, by the aged or children having difficulty in swallowing oral preparations.

For example, in the case of tablets and capsules frequently used as oral preparations, many patients of the aged or children having weak swallowing power are unwilling to take these solid preparations complaining that the drug is difficult to swallow or stops in the pharynx or gullet. Chewable tablets are not suitable for the aged or children having weak chewing power.

In the case of powders and granules, they are difficult to swallow because of their aptness to remain in the buccal cavity and, therefore, to cause an unpleasant feeling in the mouth. In some cases, the aged will be choked with powders or feel a pain or unpleasantness due to granules gotten in between false teeth. In addition, powders and granules have to be used after tearing each package, but the aged or children often have difficulty in tearing the package or spill a portion of its contents.

To take these oral preparations, it is necessary to use water, and the aged or children especially require a large volume of water in many cases because of the swallowing difficulty. However, there is a situation that it is necessary to drink water moderately, especially, before retire to bed because of the urination problem at night. In addition, in the case of patients who have to take oral preparations constantly while making daily life, water can hardly be obtained in certain cases depending on circumstances, thus sometimes entailing decline in the compliance.

Syrups and the like are regarded as desirable dosage forms for the aged or children, but the aged or children who have difficulty in measuring the necessary volume cannot be expected to use such preparations in correct dose. In addition, since there are many aged patients who can hardly take liquid preparations to mouths by themselves, such dosage forms cannot always be regarded as suitable dosage forms for the aged and children in view of the trouble during drug-taking, except for a case in which a patient can ask a nurse for a helping hand.

Taking such circumstances into consideration, attempts have been made to develop the following intrabuccally dissolving preparations as the preparation suitable for the aged and children. However, they are not practically sufficient because of the disadvantages such as (1) complex production steps and new plant and equipment investment required for the production of such preparations, (2) limitation in the application of the active ingredients and (3) difficulty in handling the preparations due to their inadequate hardness accompanied by the quick disintegration and dissolution in the buccal cavity pursued as characteristics of the preparations.

When the forthcoming social condition of advanced age is taken into consideration, development of the practical preparation which can be used easily, especially, by the aged seems to be an immediate need, because the morbidity rate of chronic diseases increases with advance in age and patients of advanced age have a tendency to take drugs for a long period of time. Also, in order to keep the quality of life, it is desirable to develop the preparation which can be easily swallowed and handled in accordance with the ability and life condition of each patient.

JP-B-58-24410 corresponding to U.S. Pat. No. 4,134,943 (the term "JP-B" as used herein means an "examined Japanese patent publication") discloses a process for the production of porous tablets having an excellent disintegration property, which comprises mixing contents of the tablet with a solvent that is inert to the contents of the tablet and that freezes at a temperature in the range of from $-30°$ C. to $+25°$ C., said solvent being used in an amount of from 5 to 80% by weight based on the total mixture, solidifying the mixture by putting the mixture in an inert cooling medium, compressing the solidified mixture at a temperature lower than the freezing point of the solvent to make the mixture into tablets, and then conducting volatilization of the solvent by means of freeze drying, spontaneous drying or the like.

JP-A-3-86837 corresponding to U.S. Pat. Nos. 5,039,540 and 5,079,018 (the term "JP-A" as used herein means an "unexamined published Japanese patent application") discloses an easily dissolvable carrier material having a sufficient strength which is obtained by allowing a composition comprising a water-soluble hydrous gel or a foam substance to contact with an anhydrous organic liquid desiccating agent such as anhydrous ethanol at a temperature of about 0° C. or lower until all of the water content is substantially removed from the composition.

Each of these production processes, however, requires complex production steps and additional manufacturing facilities such as a freeze dryer and the like, thus entailing high production cost.

JP-A-2-32014 corresponding to EP-B-345628 discloses a solid preparation in the form of molded tablets which are suitable for oral administration. However, since these tablets are obtained by preparing a wet mass using ethanol/water or water alone and drying the mass in a mold, the process to produce these tablets has poor productivity in comparison with the common production processes.

JP-A-61-15830 corresponding to EP-A-166440 discloses an antacid composition having a porous ultra-fine crystal structure, which contains an antacid agent, a sweet material for confectionery use and confectionery base containing a plasticizer. JP-A-3-209336 discloses a pharmaceutical composition which is obtained by uniformly dispersing particles of at least one pharmaceutically active compound in the crystal matrices of a crystalline sugar alcohol derived from at least one monosaccharide or polysaccharide. Each of these production processes, however, has a disadvantage in that the application of active ingredients is limited in view of the heat-stability because of the step to melt sugar components at 100° C. or higher.

In addition, though an intrabuccally dissolving pharmaceutical preparation is now commercially available from R. P Scherer under a trade name of "Zydis", it is highly costly because it requires an additional manufacturing facility such as a freeze dryer or the like due to its production by freeze drying and it requires a prolonged period of time for the production. Also, since the pharmaceutical preparation obtained by freeze drying has a week strength, it requires special cautions for its handling and, therefore, is not satisfactory for the use by the aged. For example, unlike the case of usual tablets, this preparation cannot easily be taken out by pressing the package when contained in the blister package (PTP: press through package).

The above-mentioned intrabuccally dissolving pharmaceutical preparation obtained by freeze drying (to be referred to as the "freeze-dried preparation" hereinafter) is excellent especially in disintegration and dissolution, but is not satisfactory in terms of its storage life because it does not have a sufficient hardness for keeping its dosage forms during the production steps and distribution stages.

In addition to the conventional freeze drying method, other intrabuccally dissolving pharmaceutical preparations produced by tabletting have been reported.

JP-A-5-271054 corresponding to EP-A-553777 discloses that intrabuccally dissolving tablets having an adequate strength and a porous structure which quickly disintegrate and dissolve in the buccal cavity can be obtained by preparing a mixture of an active ingredient, a saccharide and water in a sufficient amount to wet the surface of the saccharide granules, tabletting the mixture into tablets and drying the tablets.

Each of the above-mentioned intrabuccally dissolving pharmaceutical preparations obtained by tabletting (to be referred to as the "tabletted preparation" hereinafter) does not require the production steps for obtaining freeze-dried preparations and is satisfactory in terms of the storage life due to its sufficient hardness for keeping its dosage forms during the distribution stages. However, since the tabletted preparation is produced by simply subjecting a mixture or a blend to tabletting, there is still great room for the improvement of its quick disintegration and dissolution in the buccal cavity which are the characteristics of intrabuccally dissolving pharmaceutical preparations.

In addition, the following documents focused on the moldability of the saccharide and on the direct tabletting. JP-A-5-310558 discloses that, when mannitol or lactose having low binding property and poor moldability is blended with sorbitol granules having a bulk density of less than 60 g/100 ml, amounts of other additives having high moldability such as cellulose compounds, acrylic acid compounds, gelatin and the like can be reduced and solid pharmaceutical compositions having excellent disintegration property can be obtained. Similarly, JP-A-59-118058 corresponding to U.S. Pat. Nos. 4,507,511 and 4,605,794 and DE-A-1617638 disclose a preparation in which sorbitol having a particular bulk density is used. These documents may suggest that sorbitol having a particular bulk density can work as a binding agent when the direct tabletting is carried out. However, the inventions of these documents relate to an additive and a production process for obtaining tablets having an improved hardness under the usual tabletting pressure for making tablets, and their object is a production of an additive for the direct tabletting.

According to JP-A-5-170669 corresponding to EP-A-509606, moldability of lactose is improved by adding a sugar alcohol to a lactose having a high p-lactose content and drying the aqueous solution thereof by means of roller drying. However, since special saccharides are required, these processes are complex and expensive and, therefore, are not practical.

U.S. Pat. No. 4,698,101 discloses a pharmaceutical adjuvant based on fructose which is obtained by granulating fructose with an aqueous maltose solution and which can be subjected to direct tabletting.

JP-A-4-505918 based on a PCT application discloses a pharmaceutical adjuvant based on fructose which is obtained by granulating fructose with an aqueous polyol solution containing sorbitol, maltitol, lactitol, xylitol, mannitol, isomaltol, or a mixture thereof and which can be subjected to direct compression.

Although fructose is used as a core for the granulation, these documents relate to the conventional tablets, not to an intrabuccally dissolving tablets. In addition, there is a problem that, when handled usually, the granules absorb moisture due to the high hygroscopicity of fructose and, as a result, a sufficient fluidity cannot be obtained, resulting in a tendency to cause hindrance to the takeletting.

SUMMARY OF THE INVENTION

The object of the present invention is to provide (1) an intrabuccally dissolving compressed molding which shows quick disintegration and dissolution in the buccal cavity and has a hardness sufficient to keep its dosage forms, (2) a process for the production of the intrabuccally dissolving compressed molding by generally used production steps, (3) an intrabuccally dissolving compressed molding which can easily be taken without water and a process for the production thereof and (4) a useful intrabuccally dissolving compressed molding which is excellent in its industrial productivity and has the uniformity of the active ingredient content and constancy of dosage forms. Other objects and advantages of the present invention will be made apparent as the description progresses.

DETAILED DESCRIPTION OF THE INVENTION

In general, products obtained by compression such as tabletting (compressed moldings-such as tablets) have an adequate hardness as moldings. However, they are produced without taking the quick disintegration and dissolution in the buccal cavity into consideration, because the object of such products is to effect absorption of active ingredients by disintegration and dissolution of the moldings in digestive tracts through oral administration.

Accordingly, their disintegration and dissolution in the buccal cavity were not sufficient.

In order to solve the aforementioned problems, a raw material for the construction of intrabuccally dissolving compressed moldings should simultaneously have the following characteristics. Namely, it should have a quick dissolution rate in the buccal cavity and a high moldability to give an adequate hardness, when produced by compression molding such as tabletting.

First, the inventors of the present invention have examined saccharides, which are used generally as an additive such as a vehicle, as the raw material of the intrabuccal compressed moldings.

The intrabuccal dissolution time and the hardness of tablets obtained by subjecting various saccharides to tabletting under a pressure of 10 to 50 kg/cm$^2$ were measured.

As a result, a raw material simultaneously satisfying the aforementioned two characteristics was not found, but resulting in unexpectedly new finding that saccharides are divided into two groups, i.e. those showing quick dissolution rate in the buccal cavity when made into tablets and those having high moldability to give an adequate hardness.

However, when a saccharide having low moldability or a saccharide having high moldability was used alone in the compression molding, the adequate hardness and the quick disintegration and dissolution in the buccal cavity were not simultaneously obtained.

In this connection, the saccharide having low moldability was poor in the moldability as a matter of course, but showed a markedly high dissolution time of not more than about 15 seconds in the buccal cavity when made into tablets. However, a sufficient hardness was not obtained. For example, when 150 mg of the saccharide having low moldability is made into a tablet using a punch of 8 mm in diameter under a pressure of 50 kg/cm$^2$, a sufficient hardness of the tablet was not obtained.

Also, the saccharide having high moldability was excellent in the moldability as a matter of course, but its disintegration property in the buccal cavity was inferior to that of the low moldability saccharide. For example, when 150 mg of the saccharide having high moldability is made into a tablet using a punch of 8 mm in diameter under a pressure of 50 kg/cm$^2$, quick disintegration and dissolution were not achieved though a sufficient hardness of the tablet was obtained.

Moreover, quick disintegration and dissolution in the buccal cavity were not obtained when a saccharide having low moldability and a saccharide having high moldability were simply mixed (physical mixture) and tabletted. For example, when a mixture of 189 g of lactose, 10 g of maltitol and 1 g of magnesium stearate was tabletted into tablets each weighing 300 mg and having a diameter of 10 mm making use of a rotary tabletting machine using a punch of 10 mmR under a pressure of 441 kg/punch, quick disintegration and dissolution in the buccal cavity were not obtained.

Then, the present inventors have conducted extensive studies on the combination of low moldability saccharides having high dissolution with high moldability saccharides, such as on their blending ratio and blending method and the like, with the aim of finding a method which can simultaneously satisfy the two characteristics, namely, improved moldability of a low moldability saccharide to obtain an adequate hardness at the time of compression molding while keeping its quick dissolution rate. As a result, a raw material of interest was obtained by improving the defects of the saccharides having inferior moldability but excellent in disintegration and dissolution, namely low moldability saccharides and defects of the high moldability saccharides, which was achieved by subjecting a low moldability saccharide to granulation with a high moldability saccharide. Compressed moldings obtained by subjecting this raw material to a generally used compression molding step such as a tabletting step showed an adequate hardness and quick disintegration and dissolution when kept in the mouth.

In other words, the present inventors have conducted extensive studies on the intrabuccally dissolving compressed moldings with the aim of solving the aforementioned problems and, as the result, found that when a raw material obtained by granulating a low moldability saccharide showing quick disintegration and dissolution with a high moldability saccharide is subjected to a generally used molding step, the resulting moldings show quick disintegration and dissolution in the buccal cavity by merely keeping in the mouth and have an adequate hardness, so that the dosage forms do not break during the production steps and distribution stages. The present invention was accomplished on the basis of this finding.

In addition, the intrabuccally dissolving compressed moldings of the present invention are completely different from the conventional intrabuccally dissolving preparations in terms of their composition and shape, because a saccharide having high moldability was used as a binding agent in the granulation step instead of the commonly used water-soluble polymer binders such as hydroxypropylcellulose (HPC) and hydroxypropylmethylcellulose (HPMC).

Also, the present invention was accomplished on the basis of another finding that a low moldability saccharide can be used as a raw material useful for providing intrabuccally dissolving compressed moldings, preferably intrabuccally dissolving tablets by the granulation with a high moldability saccharide.

Thus, according to the present invention, there is provided an intrabuccally dissolving compressed molding capable of quickly disintegrating and dissolving in the buccal cavity, which comprises a saccharide having low moldability and another saccharide having high moldability.

The term a "saccharide having low moldability" or a "low moldability saccharide" as used herein as one of the components of the present invention means a saccharide which generally shows a hardness of 0 to 2 kg when 150 mg of the saccharide is made into a tablet using a punch of 8 mm in diameter under a pressure of 10 to 50 kg/cm$^2$. Examples of such saccharides include lactose, mannitol, glucose, sucrose, xylitol, and the like, of which lactose and mannitol are preferred. These saccharides may be used alone or as a mixture of two or more.

The term a "saccharide having high moldability" or a "high moldability saccharide" as used herein means a saccharide which generally shows a hardness of 2 kg or more when 150 mg of the saccharide is made into a tablet using a punch of 8 mm in diameter under a pressure of 10 to 50 kg/cm$^2$. Examples of such saccharides include maltose, maltitol, sorbitol, oligosaccharides and the like, of which maltose and maltitol are preferred. These saccharides may be used alone or as a mixture of two or more.

The oligosaccharide used in the present invention is not particularly limited as long as the oligosaccharide shows quick dissolution in the buccal cavity and consists of two or more of the monosaccharide residues. Oligosaccharides consisting of 2 to 6 monosaccharide residues are preferable, and the type and combination of monosaccharide residues constituting the oligosaccharide are not limited. Illustrative examples of the oligosaccharide include lactosucrose powder (e.g., Nyuka Oligo LS-55P (a product name) manufactured by Hayashibara Shoji Co., Ltd.). Oligosaccharides may be classified into homooligosaccharides and heterooligosaccharides based on the type and combination of monosaccharide residues constituting the oligosaccharide, and both of them can be used for the present invention.

The intrabuccally dissolving compressed molding of the present invention uses a saccharide having low moldability as its main component, with a blending ratio of a high moldability saccharide to the low moldability saccharide being from 2 to 20% by weight, preferably from 5 to 10% by weight.

If the blending ratio is smaller than 2% by weight, an adequate hardness of the tablets cannot be obtained, resulting in easy breakage of the tablets during their storage or transportation or when they are taken out from packages. If the blending ratio is larger than 20% by weight, the hardness of the tablets becomes excessive and the desired quick disintegration and dissolution in the buccal cavity cannot be obtained. More preferably, the blending ratio may be in the range of from 5 to 10% by weight from the view point of effective granulation operation when industrialization of the process is taken into consideration.

More preferably, granules obtained by granulating lactose and/or mannitol which has low moldability with maltose or maltitol which has high moldability in an amount of from 5 to 7.5% by weight based on the total weight of the intrabuccally dissolving compressed molding are used for the present invention. The active ingredient may be mixed by (1) a step of mixing an active ingredient with a low moldability saccharide or (2) a step of mixing an active ingredient with granules obtained by granulating a low moldability saccharide with a high moldability saccharide. Alternatively, the active ingredient may be mixed by (3) a step of mixing granules obtained by granulating a low moldability saccharide with a high moldability saccharide and granules obtained by granulating an active ingredient with a high moldability saccharide, (4) a step of granulating a low moldability saccharide with both of an active ingredient and a high moldability saccharide in any order, (5) a step of coating a low moldability saccharide (central core) with a high moldability saccharide (first layer), and then with an active ingredient (second layer), and granulating the resulting product with a high moldability saccharide, or (6) a step of coating a low moldability saccharide with an active ingredient and granulating the coated product with a high moldability saccharide. The high moldability saccharide may be added preferably in an amount of from 5 to 7.5% by weight based on the total weight of the intrabuccally dissolving compressed molding, e.g., the total weight of a low moldability saccharide or the total weight of a low moldability saccharide and an active ingredient.

The particle size distribution and the particle diameter of the granules are not particularly limited as long as the fluidity is maintained, and the usual particle size distribution for the tabletting may be employed. For example, the particle size may be from 10 μm to 1000 μm.

Active ingredients to be applied to the preparation of the present invention are not particularly limited, with their preferred examples including drugs for use in patients having difficulty in swallowing tablets, the aged and children, drugs for use in patients who require drug-taking without water while spending daily life, preparations for use in patients whose water drinking is limited and drugs for use in potions.

Illustrative examples of drugs having high utility values include:

Antacids such as sodium hydrogencarbonate, dried aluminum hydroxide gel, calcium carbonate, magnesium hydroxide, magnesium alminate silicate, synthetic aluminum silicate, synthetic hydrotalcite, magnesium aluminum hydroxide, aluminum hydroxide gel, coprecipitated product of aluminum hydroxide and sodium hydrogencarbonate, mixed dried gel of aluminum hydroxide and magnesium carbonate, coprecipitated product of aluminum hydroxide, magnesium carbonate and calcium carbonate, aluminum magnesium metasilicate, aluminum bismagnesium bismuth silicate, coprecipitated product of magnesium hydroxide and aluminum potassium sulfate, powdered oyster shell, aminoacetic acid, scopolia extract, and the like, serotonin $5HT_3$ receptor antagonists such as (R)-5-[(1-methyl-3-indolyl)carbonyl]-4,5,6,7-tetrahydro-1H-benzimidazole hydrochloride and salts thereof, ondansetron, granisetron and the like, non-steroidal anti-infammatory drugs such as indometacin, ibuprofen, ibufenac, alclofenac, diclofenac, mefenamic acid, flurbiprofen, flufenamic acid, ketoprofen, phenylbutazone, methyl salicylate and the like, steroidal anti-infammatory drugs such as cortisone, hydrocortisone, prednisolone, dexamethasone, betamethasone dipropionate, betamethasone valerate, prednisolone, triamcinolone, fluocinolone acetonide and the like, diuretic drugs such as bendroflumethiazide, polythiazide, methyclothiazide, trichlormethiazide, cyclopenthiazide, pentylhydrochlorothiazide, hydrochlorothiazide, bumetanide and the like, antipsychotic drugs such as emonapride, diazepam, nitrazepam, flunitrazepam, lorazepam, prazepam, fludiazepam, clonazepam, chlorpromazine hydrochloride, reserpine, clofluperol, trifluperidol, haloperidol, moperone, bromperidol, etizolam and the like, hypnotic drugs such as barbital, thiopental, phenobarbital, cyclobarbital, lormetazepam, triazolam, alprazolam and the like, antiepileptic drugs such as ethosuximide, sodium valproate, acetazolamide, meprobamate and the like, antiparkinsonism drugs such as chlorzoxazone, levodopa and the like, mantiemetic drugs such as metoclopramide, metoclopramide hydrochloride and the like, hormone drugs such as insulin, testosterone, methyltestosterone, progesterone, estradiol and the like, analgesic drugs such as morphine, aspirin, codeine, acetaminophen, acetanilide, aminopyrine, loxoprofen and the like, sulfa drugs such as sulfamine, sulfamonomethoxine, sulfamethizole and the like, coronary vasodilators such as nitroglycerin, isosorbide dinitrate, pentaerythrityl tetranitrate, propatylnitrate, dipyridamole, paparefine HCl and the like, $H_2$ receptor antagonists such as famotidine, cimetidine, ranitidine HCl, roxatidine acetate HCl and the like, antiarrhythmic drugs such as ajimalin, pindolol, propranolol, quinidine, amrinone, milrinone and the like, cardiotonic drugs such as caffeine, digoxin, digitoxin and the like, calcium antagonists such as nicardipine HCl diltiazem HCl nivadipine, nifedipine, nitrendipine, nisoldipine, nimodipine, niludipine and the like, antihistaminic drugs such as diphenhydramine HCl carbinoxamine, diphenylpyrallin, phenbenzamine, chlorpheniramine maleate, brompheniramine maleate, diphenylimidazol, clemizole and the like, antibiotics such as tetracycline, oxytetracycline, metacycline, doxycycline, minocycline, chloramphenicols, erythromycins, lincomycin, penicillin G, clindamycin, kanamycin, chloramphenicol, fradiomycin, streptomycin, gentamicin and the like, antitumor drugs such as 5-fluorouracil, uracil, cytarabine, floxuridine, busulfan, actinomycin, bleomycin, mitomycin and the like, antidiabetic drugs such as glibenclamide, epalrestat and the like, gout treating drugs such as allopurinol, colchicine, benzbromarone and the like, antiallergic drugs such as ketotifen fumarate, sodium cromoglicate, amlexanox and the like, antihypertensive drugs such as clonidine, atenolol, doxazosin, bisoprolol, cilazapril, lisinopril, nilvadipine, manidipine, isosorbide dinitrate, diltiazem, nicorandil, guanethidine sulfate, amosulalol HCl alacepril, delapril HCl, enalapril maleate and the like, central nervous system acting drugs such as indeloxazine HCl tiapride HCl bifemelane HCl and the like, potassium channel activator such as YM934 (2-(3,4-dihydro-2,2-dimethyl-6-nitro-2H-1,4-benzoxazin-4-yl)pyridine N-oxide), and the like, skeletal muscle relaxants such as sodium dantrolene and the like, antispasmodic drugs such as eperisone HCl tizanidine HCl butylscopolamine, attopine methylbromide and the like, antihyperlipemic drugs such as simvastatin, pravastatin sodium and the like, bronchodilators such as formoterol fumarate, salbutamol sulfate, procaterol HCl and the like, α-adrenergic receptor blockers such as tamsulosin hydrochloride, prazosin and the like, blood sugar lowering drugs, oral contraceptives, analgesic/anti-infammatory drugs such as loxoprofen and the like, digestive tract motility improving drugs such as domperidone, cisapride and the like, antigastritis and antigastric ulcer drugs such as teprenone and the like, osteoporosis treating drugs such as alfacalcidol and the like, prostatonegaly treating drugs such as chlormadinone acetate and the like, expectorants such as ambroxol and the like allergic rhinitis treating drugs such as oxatomide, ketotifen and the like, asthma treating drugs such as azelastine, procaterol, terrenadine and the like, and animal drugs having antipyretic/analgesic/anti-inflammatory activities, peptic antiulcer activities and the like and animal organ drugs for treating reproductive organ and the like.

In addition, since the intrabuccally dissolving compressed molding of the present invention is taken with disintegration and dissolution in a buccal cavity, it can be applied to the cases in which an active ingredient is absorbed in the buccal cavity as the occasion demands. In this regard, the following peptides can be exemplified in addition to the aforementioned active ingredients.

As representative peptides, various polypeptides, proteins and derivative thereof, and the like, which are liable to be degraded in the upper digestive tract but are absorbed in the lower digestive tract and show physiological effects can be used effectively as the active ingredient for the present invention. Examples of such peptides include insulin, calcitonin, angiotensin, vasopressin, desmopressin, LH-RH (luteinizing hormone-releasing hormone), somatostatin, glucagon, oxytocin, gastrin, ciclosporin, somatomedin, secretin, h-ANP (human atrial natriuretic peptide), ACTH (adrenocorticotropic hormone), MSH (melanophore-stimulating hormone), β-endorphin, muramyl dipeptide, enkephalin, neurotensin, bombesin, VIP (vasoactive intestinal polypeptide), CCK-8 (cholecystokinin-8), PTH (parathyroid hormone), CGRP (calcitonin gene related-peptide), TRH (thyrotropin-releasing hormone), endothelin, hGH (human growth hormone), and cytokines such as interleukin, interferon, colony-stimulating factor, tumor necrosis factor, etc., as well as derivatives of these peptides.

The aforementioned peptides and proteins include their pharmacologically active derivatives and homologues in addition to the naturally-derived ones. For example, the calcitonin which can be used in the present invention includes its analogues such as [Asu1,7]-eel calcitonin (elcatonin) in addition to the naturally existing products such as salmon calcitonin, human calcitonin, porcine calcitonin, eel calcitonin, and fowl calcitonin. As to insulin, human insulin, porcine insulin and bovine insulin and, in addition, their homologues such as genetic recombinants, and the like are included.

Preferable active ingredients used in the present invention are famotidine, tamsulosin hydrochloride, and YM934.

The active ingredients are not particularly limited to the above examples, and not only pharmaceutical drugs but also various other substances can be applied to the preparation of the present invention making use of its characteristic nature, which include, for example, diagnostic drugs such as a contrast medium and the like, healthy food, physiologically functional food and buccals such as a bad breath eliminating drug, a dental plaque disclosing agent and the like.

Preferably, the active ingredient may be used in an amount of 50% (w/w) or less, preferably 20% (w/w) or less, based on the total solid components (i.e., the total amount of the preparation), though it varies depending on the nature of each active ingredient to be used.

The raw material of the intrabuccally dissolving compressed moldings of the present invention is obtained by granulating a low moldability saccharide with a high moldability saccharide. The use of such a raw material renders possible production of the intrabuccally dissolving compressed moldings which quickly disintegrate and dissolve in the buccal cavity. In consequence, when the compressed moldings of the present invention are produced, the desired objects can be achieved by adding an active ingredient of interest basically at any step of the production process. The active ingredient may be present in any moiety of the intrabuccally dissolving compressed moldings of the present invention.

Though not particularly limited, illustrative examples of the active ingredient-containing raw materials include (I) a raw material which comprises granules obtained by granulating an active ingredient and a low moldability saccharide with a high moldability saccharide, (II) a raw material which comprises an active ingredient and granules obtained by granulating a low moldability saccharide with a high moldability saccharide, (III) a raw material which comprises granules obtained by granulating a low moldability saccharide with a high moldability saccharide and another granules obtained by granulating an active ingredient with a high moldability saccharide, (IV) a raw material which comprises granules obtained by granulating a low moldability saccharide with both of an active ingredient and a high moldability saccharide in any order, (V) a raw material which is obtained by coating a low moldability saccharide (central core) with a high moldability saccharide (first layer), coating the resulting product with an active ingredient (second layer) and then granulating the resulting product with a high moldability saccharide (third layer), and (VI) a raw material which is obtained by coating a low moldability saccharide with an active ingredient and granulating the coated product with a high moldability saccharide.

The active ingredient may be added to any part of the composition or at any production step.

A particularly preferred embodiment is the above construction (V) when the dose of the active ingredient is extremely small and the uniformity of the active ingredient content can hardly obtained. When the active ingredient has low moldability, the above construction (I) or (III) are preferably.

In consequence, each of the intrabuccally dissolving compressed moldings of the present invention comprises an active ingredient, a saccharide having low moldability and a saccharide having high moldability and is obtained by subjecting granules finally granulated with a saccharide having high moldability to compression molding.

In general, active ingredients which do not generate unpleasant taste at the time of their dissolution are preferably used. When a component which generates unpleasant taste is used, it is preferable to employ a proper masking treatment (cf. WO 92/09275, etc.).

In addition, when an active ingredient is desired to be made into a sustained release form, it is preferable to carry out an appropriate conventional sustained release treatment (cf. Canadian Patent No. 2,038,400-0, etc.) so that release of the active ingredient from the resulting granules can be controlled.

The solid preparation of the present invention has such a sufficient strength for handling and, therefore, can be put into practical use in the same manner as the case of usual tablets. The term "a sufficient strength for handling" as used herein means a strength which can withstand at least the usual blister packaging, and such a strength will also withstand other handling such as delivery, carrying and the like.

Hardness in the lengthwise direction of tablets may be used as an index of the strength which is applicable to the blister packaging, namely a strength necessary to take out the preparation by pushing it out of a cover sheet of usual blister packaging. Such a hardness varies depending on the size and shape of tablets and may preferably be 1.0 kg or more when the tablet has a diameter of about 8.0 mm, 1.5 kg or more for a diameter of about 10.0 mm and 2.0 kg or more for a diameter of about 12.0 mm. The solid preparation of the present invention has a sufficient strength necessary to take out the preparation from the blister packaging independent of its size.

As the strength required for the bottle packaging (a package of a container made of glass, plastics, etc. in which tablets are placed), i.e., a strength required to withstand the contact between tablets and between the tablet and the wall of the container when the bottle container is transported or carried in, the tablet may preferably have a hardness of 3 kg or more. The preparation of the present invention has a sufficient strength for transporting and carrying in the bottle packaging containing the preparation.

The hardness may be measured by, for example, the method described in the following Examples.

The term "quick disintegration and dissolution" as used herein means a practically sufficient disintegration or dissolution of the preparation by saliva in the buccal cavity without taking water. The term "practically sufficient disintegration or dissolution" means that the preparation disintegrates or dissolves in the buccal cavity generally within approximately 1 to 120 seconds, preferably within approximately 1 to 60 seconds, more preferably within approximately 1 to 40 seconds, though there are variations depending on the individual person.

The preparation of the present invention rapidly becomes brittle by saliva in the buccal cavity and gradually disintegrates or dissolves, and the disintegration or dissolution becomes more quick when an intrabuccal pressure, namely a pressure between the upper jaw and tongue, or a "licking" movement or the like is applied to the preparation.

A person of parched mouth or having a small quantity of saliva in the buccal cavity may use the preparation of the present invention with the aid of cold or hot water in an amount sufficient to wet the buccal cavity.

Also, the preparation of the present invention may be swallowed together with a small amount of water after the preparation is disintegrated or dissolved in the buccal cavity or under a partly disintegrated or dissolved condition. Even by such a way of drug-taking, merits of the preparation of the present invention such as easy swallowing, small amount of water to be used and the like can be given.

Of course, the preparation of the present invention can be taken together with water with no problems similar to the case of usual tablets. The preparation of the present invention can be used by any of these drug-taking means in accordance with each patient's choice or condition, provided that there are no limitations with respect to the active ingredient contained therein.

(Production process)

The following describes the processes for the production of the intrabuccally dissolving compressed moldings of the present invention in detail, but these processes do not restrict the scope of the present invention.

First process

An active ingredient is added to a low moldability saccharide and the resulting mixture is granulated with a high moldability saccharide. In the resulting granules, granules of the active ingredient and granules of the low moldability saccharide are linked together with the high moldability saccharide. Preferably, the resulting granules may further be granulated with the high moldability saccharide. The resulting granules are subjected to compression molding to obtain, for example, intrabuccally dissolving tablets.

Second process

A low moldability saccharide is granulated with a high moldability saccharide. The resulting granules are mixed with an active ingredient, and the resulting mixture is subjected to compression molding to obtain, for example, intrabuccally dissolving tablets.

Third process

A low moldability saccharide is granulated with a high moldability saccharide to obtain granules. Separately, an active ingredient is granulated with a high moldability saccharide to obtain granules. These granules are mixed and subjected to compression molding to obtain, for example, intrabuccally dissolving tablets.

Fourth process

A low moldability saccharide is granulated with both of an active ingredient and a high moldability saccharide in any order. The resulting granules are subjected to compression molding to obtain, for example, intrabuccally dissolving tablets.

Fifth process

A low moldability saccharide (central core) is coated with a high moldability saccharide (first layer) and then coated with an active ingredient (second layer), and the resulting product is granulated with a high moldability saccharide (third layer). The resulting granules are subjected to compression molding to obtain, for example, intrabuccally dissolving tablets.

Sixth process

A low moldability saccharide is coated with an active ingredient and the coated product is granulated with a high moldability saccharide. The resulting granules are subjected to compression molding to obtain, for example, intrabuccally dissolving tablets.

The granulation may be carried out making use of, for example, a fluidized bed granulator (manufactured by Ohgawara Seisakusho), a vertical mixer (manufactured by San-ei Seisakusho), an agitated granulating machine (manufactured by Fukae Kogyo) or the like, by mixing an active agent with a low moldability saccharide and other additive agents and coating and/or granulating the resulting mixture using an aqueous solution of a high moldability saccharide as a binding agent. More illustratively, when a fluidized bed granulator is used, granulation is carried out to obtain granules having a desired particle size in accordance with the generally used operation conditions, for example, under a spray pressure of 0.3 to 2 kg/cm$^2$ and at a temperature of 20 co 30° C. In this instance, the effects of the present invention are further improved when fine granule coating is carried out as a pretreatment of the granulation by means of a side spraying using a portion of the binding agent.

The compression molding may be carried out by tabletting using a tabletting machine generally used for the molding of tablets, such as a single tabletting machine (manufactured by Kikusui Seisakusho), a rotary tabletting machine (manufactured by Hata Seisakusho) or the like. The molding pressure at the time of tabletting may optionally be selected depending on the hardness and dissolution property of the resulting moldings and, therefore, is not particularly limited.

With respect to the intrabuccally dissolving compressed molding of the present invention, the hardness of the tablet after tabletting can be further improved while maintaining the dissolution property by appropriately utilizing the step comprising spraying a physiologically acceptable organic solvent or water, and drying; a step comprising humidity treatment and drying; or the like.

The preparation of the present invention may contain various additive agents generally used in the production of tablets as long as they do not spoil the effects of the present invention.

Such additive agents include disintegrating agents, binding agents, souring agents, vesicants, artificial sweeteners, perfumes, lubricants, coloring agents and the Illustrative examples of disintegrating agents include starches such as corn starch, potato starch and the like, as well as carboxymethylcellulose calcium and the like. Illustrative examples of binding agents include powdered acacia, gelatin, pullulan and the like.

Illustrative examples of souring agents include citric acid, tartaric acid, malic acid and the like. illustrative examples of vesicants include sodium bicarbonate and the like. illustrative examples of artificial sweeteners include saccharin sodium, glycyrrhizin dipotassium, aspartame, stevia, thaumatin and the like.

Illustrative examples of perfumes include lemon, lemon lime, orange, menthol and the like. illustrative examples of lubricants include magnesium stearate, sucrose fatty acid ester, polyethylene glycol, talc, stearic acid and the like. Illustrative examples of coloring agents include food dyes such as Food Yellow No. 5, Food Red No. 2, Food Blue No. 2 and the like, as well as food lake dyes, red iron oxide and the like.

These additive agents may be used alone or as a mixture of two or more in an appropriate amount at an optional step in the production process of the intrabuccally dissolving compressed moldings, for example, when an active ingredient is mixed with a low moldability saccharide, when a coating solution prepared by dissolving an active ingredient together with a high moldability saccharide in water is mixed, or at a step before or after these steps.

With regard to the effects of the present invention, the intrabuccally dissolving compressed moldings show excellent dissolution inherent to low moldability saccharides and excellent disintegration resulting from the high dissolution, because each of the moldings uses a saccharide having low moldability as its main component, with a blending ratio of a high moldability saccharide to the low moldability saccharide of from 2 to 20% by weight, preferably from 5 to 10% by weight, while the use of the high moldability saccharide gives other useful physical properties such as the adequate hardness and the like, which cannot be found in the conventional intrabuccally dissolving compressed moldings.

The intrabuccally dissolving compressed moldings of the present invention are produced through conventionally used production steps, namely granulation and tabletting, without employing a freeze drying step which is essential for the production of the conventional intrabuccally dissolving compressed moldings. In consequence, the moldings of the present invention can be produced economically with a high industrial productivity, because special facilities for freeze drying are not required.

In addition, the adequate hardness of the intrabuccally dissolving compressed moldings of the present invention renders possible easy handling of the moldings during their production steps and distribution stages.

The intrabuccally dissolving compressed molding of the present invention can be applied to the cases in which an active ingredient is absorbed in the buccal cavity as the occasion demands.

Hardness test can be carried out in the usual way, for example, by subjecting test samples to a Schleuniger tablet hardness meter (manufactured by Schleuniger).

EXAMPLES

The following examples are provided to further illustrate the present invention. It is to be understood, however, that the examples are for purpose of illustration only and are not intended as a definition of the limits of the present invention.
(Test Examples)

In order to describe the effects of the present invention further in detail, properties of the tablets obtained in Examples were measured in the following manner.
(1) Hardness test The hardness was measured using a tablet hardness meter (manufactured by Schleuniger). Each test was carried out 3 to 10 times (n=3 to 10), and the average value was used in the following.
(2) Disintegration dissolution test in the buccal cavity without water A sample of compressed moldings was put into the buccal cavity of healthy male adult volunteers without water (not holding water in the mouth) to measure the time required for the complete disintegration and dissolution of the sample by saliva in the buccal cavity.
(3) Disintegration test Disintegration was measured in accordance with the disintegration test described in *The Japanese Pharmacopoeia*, 12th revision, (to be referred to as "JP disintegration test" hereinafter). Each test was carried out 6 times, and the average value was used in the following.

Since the physicochemical properties and the amount of the active ingredient influence the hardness, the dissolution time in the buccal cavity of the moldings of the present invention only in rare cases, the active ingredient was not used in some of the following Examples.

Unless otherwise indicated, all parts, percentages, ratios, etc. hereinafter are by weight.

EXAMPLE 1

A 20 g portion of maltose (manufactured by Hayashibara Shoji) was dissolved in 180 g of water. Using the resulting aqueous solution of maltose, 400 g of mannitol (manufactured by Towa Kasei Kogyo) was subjected to granulation making use of a fluidized bed granulator (manufactured by Ohgawara Seisakusho). In this case, fine particle coating was carried out under a spray pressure of 3 kg/cm² for the first 10 g of maltose and then granulation was carried out under a spray pressure of 0.5 kg/cm². After drying, magnesium stearate was blended in an amount of 0.5% and the resulting granules (mean particle diameter: 184 μm) were applied to a rotary tabletting machine (manufactured by Hata Seisakusho) using a punch of 10 mmR having a diameter of 10 mm to obtain tablets each weighing 300 mg. The hardness test was repeated 3 times (n=3).

EXAMPLE 2

The procedure of Example 1 was repeated except that maltitol (manufactured by Towa Kasei Kogyo) was used instead of maltose. The mean particle diameter of the granules was 158 μm.

EXAMPLE 3

The procedure of Example 1 was repeated except that sorbitol (manufactured by Towa Kasei Kogyo) was used instead of maltose. The mean particle diameter of the granules was 146 μm.

EXAMPLE 4

The procedure of Example 1 was repeated except that lactose (manufactured by Domo Milk) was used instead of mannitol. The hardness test was repeated 3 times (n=3). The mean particle diameter of the granules was 136 μm.

EXAMPLE 5

The procedure of Example 1 was repeated except that an oligosaccharide (Nyuka Oligo LS-55P, manufactured by Hayashibara Shoji) was used instead of maltose. The hardness test was repeated 3 times (n=3). The mean particle diameter of the granules was 192 μm.

EXAMPLE 6

After mixing 200 g of lactose with 200 g of mannitol, granulation was carried out making use of a fluidized bed granulator using 20 g of maltitol dissolved in 80 g of water. In this case, granulation was carried out under a spray pressure of 0.5 kg/cm². After drying, magnesium stearate was blended in an amount of 0.5% and the resulting granules (mean particle diameter: 202 μm) were applied to a rotary tabletting machine using a punch of 10 mmR having a diameter of 10 mm to obtain tablets each weighing 300 mg. The hardness test was repeated 3 times (n=3).

TABLE 1

| Example | Ratio of Low moldability sugar/ High moldability sugar | Tabletting pressure (kg/punch) | Hardness (kg) | Time *1 (sec) |
| --- | --- | --- | --- | --- |
| 1 | mannitol:maltose = 20:1 | 303 | 5.9 | 15 |
| 4 | lactose:maltose = 20:1 | 334 | 5.3 | 15 |
| 5 | mannitol:oligosaccharide = 20:1 | 441 | 3.6 | 20 |
| 6 | mannitol:lactose:maltose = 10:10:1 | 388 | 3.7 | 16 |

*1 disintegration-dissolution time in the buccal cavity

EXAMPLE 7

Granules were prepared by repeating the procedure of Example 1 except that glucose (manufactured by Nippon Shokuhin Kako) was used instead of mannitol. After drying, the granules (mean particle diameter: 295 μm) were applied to an oil press machine using a punch of 10 mmR having a diameter of 10 mm under a pressure of 20 kg/cm² to obtain tablets each weighing 300 mg.

EXAMPLE 8

The procedure of Example 7 was repeated except that xylitol (manufactured by Towa Kasei Kogyo) was used instead of glucose.

EXAMPLE 9

The procedure of Example 7 was repeated except that sucrose (manufactured by Nisshin Seito) was used instead of glucose. The mean particle diameter of the granules was 355 μm.

EXAMPLE 10

After mixing 2.832 kg of mannitol, 2.832 kg of lactose, 1.0 kg of famotidine, and 0.225 kg of aspartame, granulation was carried out making use of a fluidized bed granulator (manufactured by Ohgawara Seisakusho) using 2.5 kg of a 15% maltose aqueous solution. In this case, fine particle coating was carried out under a spray pressure of 4.0 kg/cm² for the first 1.0 kg of maltose aqueous solution and then granulation was carried out. The inclusion complex was prepared using 77.8 g of β-cyclodextrin (referred to as "β-CD" hereinafter) and 8.6 g of menthol in water, and this suspension was sprayed to the resulting granules in the same manner. After drying, calcium stearate was blended in an amount of 1% and the resulting granules (mean particle diameter: 102 μm) were applied to a rotary tabletting machine using a punch of 9.6 mmR having a diameter of 8 ram under a pressure of 84 kg/punch to obtain tablets each weighing 150 mg. The resulting tablets showed a disintegration dissolution time of 15 seconds in the buccal cavity and a hardness (n=5) of 3.9 kg.

EXAMPLE 11

After mixing 20 g of famotidine, 270 g of lactose, 40 g of mannitol, 8 g of aspartame, and 2 g of sodium citrate, granulation was carried out making use of a fluidized bed granulator (manufactured by Ohgawara Seisakusho) using 16 g of maltose dissolved in 144 g of water. In this case, fine particle coating was carried out under a spray pressure of 3 kg/cm² for the first 8 g of maltose and then granulation was carried out under a spray pressure of 0.5 kg/cm². The inclusion complex was prepared using 0.34 g of menthol and 2.46 g of β-CD in hot water, and this suspension was sprayed to the resulting granules in the same manner. After drying, magnesium stearate was blended in an amount of 0.5% and the resulting granules (mean particle diameter: 198 μm) were applied to a rotary tabletting machine (manufactured by Hata Seisakusho) using a punch of 10 mmR having a diameter of 10 mm under a pressure of 133 kg/punch to obtain tablets each weighing 355.3 mg. The resulting tablets showed a disintegration dissolution time of 15 seconds in the buccal cavity and a hardness (n=3) of 3.8 kg.

EXAMPLE 12

A 21 g portion of maltose was dissolved in 189 g of water. Using the resulting aqueous solution of maltose, a mixture of 396.9 g of mannitol and 3.5 g of glibenclamide was subjected to granulation making use of a fluidized bed granulator. In this case, fine particle coating was carried out under a spray pressure of 3 kg/cm² for the first 8 g of maltose and then granulation was carried out under a spray pressure of 0.6 kg/cm². After drying, magnesium stearate was blended in an amount of 0.5% and the resulting granules (mean particle diameter: 127 μm) were applied to a rotary tabletting machine using a punch of 10 mmR having a diameter of 10 mm under a pressure of 319 kg/punch to obtain tablets each weighing 300 mg. The resulting tablets showed a disintegration dissolution time of 15 seconds in the buccal cavity and a hardness (n=10) of 3.0 kg.

EXAMPLE 13

Using 10 g of maltose dissolved in 90 g of water, 400 g of mannitol was subjected to granulation making use of a fluidized bed granulator (manufactured by Ohgawara Seisakusho). In this case, fine particle coating was carried out under a spray pressure of 3 kg/cm². After drying, the resulting granules (mean particle diameter: 98 μm) were applied to an oil press machine using a punch of 10 mmR having a diameter of 10 mm under a pressure of 50 kg/cm² to obtain tablets each weighing 300 mg. The resulting tablets showed a disintegration dissolution time of 15 seconds in the buccal cavity and a hardness (n=3) of 4.8 kg.

EXAMPLE 14

A 35 g portion of maltose was dissolved in 140 g of water. Using the resulting aqueous solution of maltose, 350 g of mannitol was subjected to granulation making use of a fluidized bed granulator (manufactured by Ohgawara Seisakusho). In this case, fine particle coating was carried out under a spray pressure of 3 kg/cm² for the first 16 g of maltose and then granulation was carried out under a spray pressure of 0.5 kg/cm². After drying, magnesium stearate was blended in an amount of 0.5% and the resulting granules (mean particle diameter: 329 μm) were applied to a rotary tabletting machine using a punch of 10 mmR a diameter of 10 mm to obtain tablets each weighing 300 mg. The resulting tablets showed a disintegration dissolution time of 18 seconds in the buccal cavity and a hardness (n=3) of 3.0 kg.

EXAMPLE 15

Using two aqueous solutions of maltose, a mixture of 4 kg of mannitol and 4 kg of lactose was subjected to granulation making use of a fluidized bed granulator (manufactured by Ohgawara Seisakusho). In this case, fine particle coating was carried out under a spray pressure of 3 kg/cm² using 2.0 kg of a 10% (w/w) maltose aqueous solution and then granulation was carried out under a spray pressure of 1.5 kg/cm² using 1.3 kg of a 30% (w/w) maltose aqueous solution. After drying, 240.4 g of the resulting granules (mean particle diameter: 140 μm) were mixed with 8.3 g of famotidine and 1.25 g of magnesium stearate, and the resulting mixture was applied to a rotary tabletting machine using a punch of 10 nmR having a diameter of 10 mm to obtain tablets each weighing 300 mg. The resulting tablets showed a disintegration dissolution time of 20 seconds in the buccal cavity and a hardness (n=5) of 3.6 kg.

EXAMPLE 16

Using two aqueous solutions of maltose, 8 kg of mannitol was subjected to granulation making use of a fluidized bed granulator (FLO-5, manufactured by Ohgawara Seisakusho). In this case, fine particle coating was carried out under a spray pressure of 2.5 kg/cm² using 2.0 kg of a 10% (w/w) maltose aqueous solution and then granulation was carried out under a spray pressure of 1.5 kg/cm² using 2.0 kg of a 20% (w/w) maltose aqueous solution.

Separately, 500 g of acetaminophen was subjected to granulation making use of a fluidized bed granulator (Unigrat, manufactured by Ohgawara Seisakusho) using 25 g of maltose as a 10% maltose aqueous solution.

A 63 g portion of the resulting acetaminophen granules (mean particle diameter: 120 μm) were mixed with 235.5 g of the previously prepared mannitol granules (mean particle diameter: 134 μm) and 1.5 g of magnesium stearate, and the resulting mixture was applied to a rotary tabletting machine using a punch of 10 mmR having a diameter of 10 mm to obtain tablets each weighing 300 mg. The resulting tablets showed a disintegration dissolution time of 20 seconds in the buccal cavity and a hardness (n=5) of 4.1 kg.

EXAMPLE 17

Using two aqueous solutions of maltose, a mixture consisting of 487.5 g of mannitol and 162.5 g of lactose was subjected to granulation making use of a fluidized bed granulator (Unigrat, manufactured by Ohgawara Seisakusho). In this case, fine particle coating was carried out under a spray pressure of 3 kg/cm² using 130 g of a 10% (w/w) maltose aqueous solution and then coating was carried out under the same conditions using a solution which had been prepared by dissolving 138 mg of YM934 (2-(3,4-dihydro-2,2-dimethyl-6-nitro-2H-1,4-benzoxazin-4-yl)pyridine N-oxide) in 50 ml of methanol. Thereafter, granulation was carried out under a spray pressure of 1.3 kg/cm² using 98 g of a 20% (w/w) maltose aqueous solution.

After drying, 628.1 g of the resulting granules (mean particle diameter: 161 μm) were mixed with 1.89 g of magnesium stearate, and the resulting mixture was applied to a rotary tabletting machine using a punch of 10 mmR having a diameter of 10 mm to obtain tablets each weighing 294 mg. The resulting tablets showed a disintegration time of 25 seconds by the JP disintegration test and a hardness (n=10) of 4.5 kg.

EXAMPLE 18

Using 2.67 kg of a 15% (w/w) maltose aqueous solution, 8 kg of mannitol was subjected to granulation making use of a fluidized bed granulator (FLO-5, manufactured by Ohgawara Seisakusho), and dried. In this case, fine particle coating was carried out under a spray pressure of 3.0 kg/cm² for the first 1.0 kg of the maltose aqueous solution and then granulation was carried out. Separately, 500 g of calcium carbonate was suspended in a solution which had been prepared by dissolving 50 g of maltose in 367 g of water. The resulting suspension was spray dried using a spray drying machine manufactured by Ohgawara Kakoki. A 110 g portion of the resulting spray-dried product, 132 g of the previously prepared mannitol granules, 20 g of magnesium hydroxide and 1.2 g of magnesium stearate were mixed, and the resulting mixture was applied to a rotary tabletting machine using a punch of 11 mmR having a diameter of 11 nun under a pressure of 154 kg/punch to obtain tablets each weighing 525 mg. The resulting tablets showed a dissolution time of 25 seconds in the buccal cavity and a hardness (n=5) of 3.7 kg.

EXAMPLE 19

A 10 mg portion of salmon calcitonin, 100 mg of gelatin, and 890 mg of mannitol were mixed in a mortar to prepare a powder having 1% salmon calcitonin. This powder was mixed with 8 g of the mannitol granules prepared in Example 18, and the resulting mixture was applied to an oil press machine using a punch of 9.6 mmR having a diameter of 8 mm under a pressure of 20 kg/cm$^2$ to obtain tablets each weighing 112.5 mg (corresponding to 500 IU salmon calcutonin). The resulting tablets showed a dissolution time of 10 seconds in the buccal cavity and a hardness (n=5) of 5.9 kg.

While the invention has been described in detail and with reference to specific examples thereof, it will be apparent to one skilled in the art that various changes and modifications can be made without departing from the spirit and scope thereof.

What is claimed is:

1. An intrabuccally dissolving compressed molding showing quick disintegration and dissolution in the buccal cavity, which comprises granules comprising a saccharide having low moldability having been granulated with a saccharide having high moldability.

2. The intrabuccally dissolving compressed molding according to claim 1, wherein said molding further comprises an active ingredient.

3. The intrabuccally dissolving compressed molding according to claim 2, wherein said saccharide having low moldability is at least one saccharide selected from the group consisting of lactose, mannitol, glucose, sucrose, and xylitol.

4. The intrabuccally dissolving compressed molding according to claim 2, wherein said saccharide having high moldability is at least one saccharide selected from the group consisting of maltose, maltitol, sorbitol and an oligosaccharide.

5. The intrabuccally dissolving compressed molding according to claim 2, wherein the blending ratio of said saccharide having high moldability to said saccharide having low moldability is 2 to 20% by weight.

6. The intrabuccally dissolving compressed molding according to claim 2, wherein said molding is a tablet.

7. A process for producing intrabuccally dissolving compressed moldings showing quick disintegration and dissolution in the buccal cavity, which comprises granulating a saccharide having low moldability with a saccharide having high moldability and subjecting the resulting granules to compression molding.

8. The process for producing intrabuccally dissolving compressed moldings according to claim 7, wherein said molding further comprises an active ingredient.

9. The process for producing intrabuccally dissolving compressed moldings according to claim 8, which comprises granulating the active ingredient and the saccharide having low moldability with the saccharide having high moldability, and subjecting the resulting granules to compression molding.

10. The process for producing intrabuccally dissolving compressed moldings according to claim 8, which comprises granulating the saccharide having low moldability with the saccharide having high moldability, mixing the resulting granules with the active ingredient, and subjecting the resulting mixture to compression molding.

11. The process for producing intrabuccally dissolving compressed moldings according to claim 8, which comprises granulating the saccharide having low moldability with the saccharide having high moldability to obtain first granules, granulating the active ingredient with a saccharide having high moldability to obtain second granules, mixing the first granules and the second granules, and subjecting the resulting mixture to compression molding.

12. The process for producing intrabuccally dissolving compressed moldings according to claim 8, which comprises granulating the saccharide having low moldability with both of the active ingredient and the saccharide having high moldability in any order, and subjecting the resulting granules to compression molding.

13. The process for producing intrabuccally dissolving compressed moldings according to claim 12, which comprises coating the saccharide having low moldability, as a central core, with the saccharide having high moldability, as a first layer, coating the resulting product with the active ingredient, as a second layer, coating the resulting product with a saccharide having high moldability, as a third layer, thereby obtaining a three layer structure coat, and subjecting the resulting granules to compression molding.

14. The process for producing intrabuccally dissolving compressed moldings according to claim 8, wherein said saccharide having low moldability is at least one saccharide selected from the group consisting of lactose, mannitol, glucose, sucrose, and xylitol.

15. The process for producing intrabuccally dissolving compressed moldings according to claim 8, wherein said saccharide having high moldability is at least one saccharide selected from the group consisting of maltose, maltitol, sorbitol and an oligosaccharide.

16. The process for producing intrabuccally dissolving compressed moldings according to claim 8, which further comprises a step of adding at least one additive agent selected from the group consisting of a disintegrating agent, a binding agent, a souring agent, a vesicant, an artificial sweetener, a perfume, a lubricant and a coloring agent.

17. The process for producing intrabuccally dissolving compressed moldings according to claim 8, wherein said compression molding is tabletting.

18. A method of dissolving in a buccal cavity an intrabuccally dissolving compressed molding showing quick disintegration and dissolution in the buccal cavity which comprises a saccharide having low moldability granulated with a saccharide having high moldability.

19. The process according to claim 7, wherein said granulating of the saccharide having low moldability is carried out using an aqueous solution of the saccharide having high moldability.

20. The process according to claim 7, which further comprises the step of drying the granules before compression molding.

21. The process according to claim 7, which further comprises the steps of subjecting the molding after compression molding to a humidity treatment, and drying the molding.

22. The process according to claim 7, which further comprises the steps of spraying a pharmaceutically acceptable organic solvent or water onto the molding after compression molding and drying the molding.

23. An intrabuccally dissolving compressed molding showing quick disintegration and dissolution in the buccal cavity producible by the steps of granulating a saccharide having low moldability with a saccharide having high moldability and subjecting the resulting granules to compression molding.

24. The intrabuccally dissolving compressed molding according to claim 23, wherein said molding further comprises an active ingredient.

25. The intrabuccally dissolving compressed molding according to claim 24, which is producible by granulating the active ingredient and the saccharide having low moldability with the saccharide having high moldability, and subjecting the resulting granules to compression molding.

26. The intrabuccally dissolving compressed molding according to claim 24, which is producible by granulating the saccharide having low moldability with the saccharide having high moldability, mixing the resulting granules with the active ingredient, and subjecting the resulting mixture to compression molding.

27. The intrabuccally dissolving compressed molding according to claim 24, which is producible by granulating the saccharide having low moldability with the saccharide having high moldability to obtain first granules, granulating the active ingredient with a saccharide having high moldability to obtain second granules, mixing the first granules and the second granules, and subjecting the resulting mixture to compression molding.

28. The intrabuccally dissolving compressed molding according to claim 24, which is producible by granulating the saccharide having low moldability with both the active ingredient and the saccharide having high moldability, in any order, and subjecting the resulting granules to compression molding.

29. The intrabuccally dissolving compressed molding according to claim 28, which is producible by coating the saccharide having low moldability, as a central core, with the saccharide having high moldability, as a first layer, coating the resulting product with the active ingredient, as a second layer, coating the resulting product with a saccharide having high moldability, as a third layer, thereby obtaining a three layer structure coat, and subjecting the resulting granules to compression molding.

30. The intrabuccally dissolving compressed molding according to claim 24, wherein said saccharide having low moldability is at least one saccharide selected from the group consisting of lactose, mannitol, glucose, sucrose and xylitol.

31. The intrabuccally dissolving compressed molding according to claim 24, wherein the saccharide having high moldability is at least one saccharide selected from the group consisting of maltose, maltitol, sorbitol and an oligosaccharide.

32. The intrabuccally dissolving compressed molding according to claim 24, wherein said molding further comprises at least one additive agent selected from the group consisting of a disintegrating agent, a binding agent, a souring agent, a vesicant, an artificial sweetener, a perfume, a lubricant and a coloring agent.

33. The intrabuccally dissolving compressed molding according to claim 23, wherein said compression molding is tabletting.

* * * * *